(12) United States Patent
Sinofsky et al.

(10) Patent No.: US 6,605,055 B1
(45) Date of Patent: Aug. 12, 2003

(54) BALLOON CATHETER WITH IRRIGATION SHEATH

(75) Inventors: Edward L. Sinofsky, Dennis, MA (US); Lincoln S. Baxter, Centerville, MA (US)

(73) Assignee: CardioFocus, Inc., Norton, MA (US)

( * ) Notice: Subject to any disclaimer, the term of this patent is extended or adjusted under 35 U.S.C. 154(b) by 91 days.

(21) Appl. No.: 09/660,601

(22) Filed: Sep. 13, 2000

(51) Int. Cl.[7] ............................................. A61M 29/00
(52) U.S. Cl. ............................ 604/96.01; 604/101.02; 604/103.01
(58) Field of Search .................. 604/96.01, 103.01, 604/103.02; 607/101.02, 101.03

(56) References Cited

U.S. PATENT DOCUMENTS

| | | | | |
|---|---|---|---|---|
| 5,213,576 A | * | 5/1993 | Abiuso et al. | 604/103.01 |
| 5,226,880 A | * | 7/1993 | Martin | 604/96.01 |
| 5,242,398 A | | 9/1993 | Knoll et al. | 604/101 |
| 5,336,178 A | * | 8/1994 | Kaplan et al. | 604/103.01 |
| 5,421,826 A | * | 6/1995 | Crocker et al. | 604/103.01 |
| 5,562,620 A | * | 10/1996 | Klein et al. | 604/103.01 |
| 5,575,772 A | | 11/1996 | Lennox | 604/96 |
| 5,653,734 A | | 8/1997 | Alt | 607/5 |
| 5,700,243 A | * | 12/1997 | Narciso, Jr. | 604/102 |
| 5,716,373 A | | 2/1998 | Wolvek et al. | 606/194 |
| 5,779,670 A | | 7/1998 | Bidwell et al. | 604/172 |
| 5,800,392 A | | 9/1998 | Racchini | 604/96 |
| 5,843,033 A | * | 12/1998 | Kopiak et al. | 604/103.01 |
| 5,860,966 A | | 1/1999 | Tower | 606/1 |
| 5,904,147 A | | 5/1999 | Conlan et al. | 128/899 |
| 5,938,660 A | | 8/1999 | Swartz et al. | 606/45 |
| 5,947,959 A | | 9/1999 | Sinofsky | 606/15 |
| 5,980,485 A | | 11/1999 | Grantz et al. | 604/96 |
| 5,997,527 A | | 12/1999 | Gumicio et al. | 604/892 |
| 6,012,457 A | | 1/2000 | Lesh | 128/898 |
| 6,024,740 A | | 2/2000 | Lesh et al. | 606/34 |
| 6,135,991 A | * | 10/2000 | Muni et al. | 604/96.01 |
| 6,159,195 A | * | 12/2000 | Ha et al. | 604/500 |

* cited by examiner

*Primary Examiner*—Ronald Capossela
(74) *Attorney, Agent, or Firm*—Thomas J. Engellenner; Lisa J. Michaud; Nutter McClennen & Fish LLP

(57) ABSTRACT

The present invention is directed to a balloon catheter having an irrigation sheath. The balloon catheter has a first expandable membrane forming an occluding balloon. A second membrane forms a sheath about the occluding balloon for providing irrigation to a body lumen. Fluid is provided to the occluding balloon to position the catheter and/or occlude the flow of blood. Fluid is then passed through the sheath to irrigate the target site. In one embodiment of the present invention, the sheath has a plurality of fluid releasing pores.

9 Claims, 5 Drawing Sheets

BALLOON CATHETER WITH IRRIGATION SHEATH

BACKGROUND OF THE INVENTION

The present invention relates to catheters for diagnosis of, or delivery of localized therapy to, a target region of a body lumen, and, in particular, to balloon structures for positioning a catheter or similar device within the heart.

Catheterization is a type of procedure performed for a variety of purposes, including diagnostic, interventional, and other therapeutic procedures. In catheterization techniques, a long tubular catheter is introduced into the body through a puncture site. It is then passed to a target site, usually through the circulatory system. The therapeutic procedures are usually accomplished at the distal end of the catheter by manipulation of the proximal portion of the catheter remaining outside the body, or by introducing instruments or therapeutic agents into the catheter body at the proximal end for passage through the catheter to the target site.

During many of these procedures, it is necessary to keep the distal end of the catheter in a relatively stable position to perform the desired procedure. In order to ensure that a catheter is maintained in the proper position, it is common to use an expandable balloon disposed near the distal end of the catheter shaft. These catheters typically include a lumen that extends from the proximal end to the balloon end and provide fluid to the balloon for its inflation. Inflation of the balloon causes the balloon to engage the wall of a lumen. The procedure is then performed. Once completed, the fluid is removed from the balloon, thereby deflating the balloon and allowing the catheter to be removed.

Balloon catheters are commonly used to facilitate a number of percutaneous medical treatments such as pressure monitoring, cardiac output and flow monitoring, angioplasty, artificial vaso-occlusion, cardiac support, and cardiac ablation. Such catheters can also deliver therapeutic agents or energy once a target region is identified. Cardiac ablation catheters, for example, delivery energy, which may be in the form of heat, electric current or radiation, in order to eliminate (i.e. "ablate") the source of a cardiac arrhythmia. Such catheters typically include an optical apparatus contained within the catheter. The catheter can also include other structures, such as a lumen through which pharmaceutics, biologics, or photoactivatable agents are delivered, as well as mapping electrodes, and/or a sampling system for sampling a tissue or fluid specimen.

Although various types of balloon anchored catheters have been proposed, they often suffer from one or more limitations. A serious drawback to using balloon catheters is that the balloon can cause a total block to the flow of blood through the lumen, depriving tissue of needed blood. This can cause tissue damage, even when the procedure is performed expediently. In addition, blood that is trapped in the occluded area can clot and cause thrombosis.

Consequently, there is a need for better balloon catheter devices that can provide irrigation to reduce the chance of clotting, and/or locally clear blood from a target site without necessarily causing a total blockage of blood flow.

SUMMARY OF THE INVENTION

The present invention is directed to a balloon catheter having an irrigation sheath. The structure can include two expandable membranes disposed about a catheter. The first inner membrane is generally or substantially sealed and serves as a balloon to position the device within a lumen. This balloon structure, when filled with fluid, expands and is engaged in direct contact with the tissue. A second (outer) membrane is not completely sealed and instead provides a pathway for delivery of fluid at the treatment site.

In one embodiment, the outer membrane is an irrigation sheath, partially disposed about the occluding inner balloon, and provides irrigation at a treatment site (e.g. so that blood can be cleared from an ablation site). The entire structure can be deflated by applying a vacuum which removes the fluid from the inner balloon. Once fully deflated, the catheter can be easily removed from the body lumen.

In another embodiment of the present invention, the distal end of the sheath, which provides fluid to the treatment site, is position to direct fluid toward the tissue being ablated. In yet another embodiment, the sheath contains fluid releasing pores.

One advantage of the present invention is that irrigation provided by the second membrane reduces hematocrit and the chance of clotting. In phototherapy applications, the removal of blood from the treatment site allows for the unobstructed and uniform delivery of ablative energy. In addition, the irrigating fluid cools the surface of the target site, thereby preventing overheating or burning of the tissue, or coagulation. Moreover, the use of two membranes permits the delivery of two separate fluids, a physiologically compatible fluid and an inflation fluid.

BRIEF DESCRIPTION OF THE DRAWINGS

The invention will be more fully understood from the following detailed description taken in conjunction with the accompanying drawings, in which.

DETAILED DESCRIPTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Figure 1:
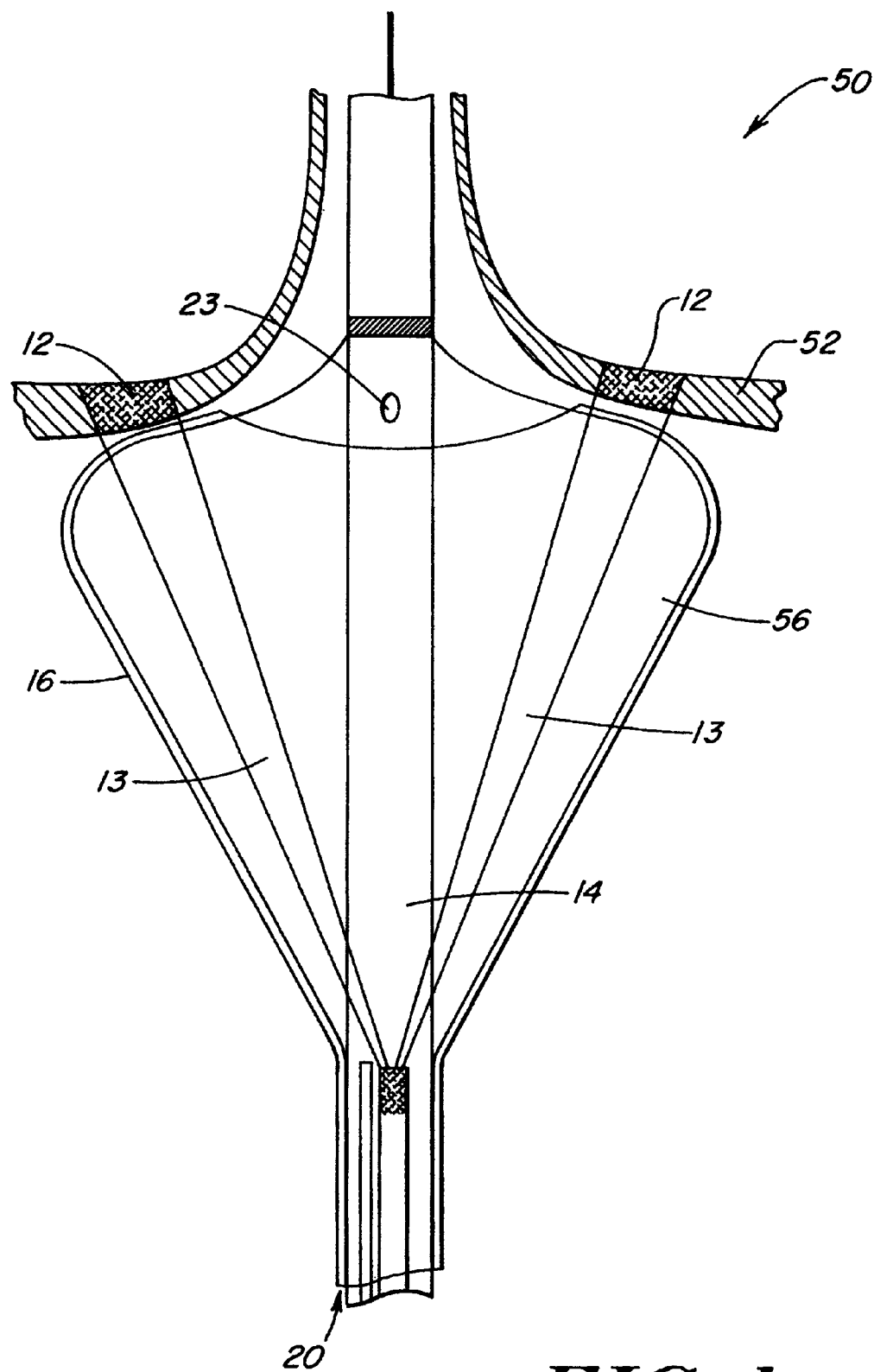
FIG. 1 is a schematic, cross-sectional view of a balloon catheter apparatus having an irrigation sheath according to the invention.

In FIG. 1, a balloon catheter 50 for cardiac ablation is shown including a primary balloon member 56 disposed about a catheter 14 for inflation (via port 23) within the body (e.g., with the heart) to provide a transmission waveguide for projecting radiation 13 to the ablation site 12. The primary balloon member 56 is generally or substantially sealed and can be inflated to position the catheter 14 within a lumen. The catheter 14 is typically an elongated hollow instrument having at least one lumen 23. The primary balloon 56 is shown engaged in direct contact with a body lumen 52 (e.g.

a pulmonary vein). A sheath 16 is partially disposed about the primary balloon member 56 for providing irrigation (via conduit 20) to the body lumen. Primary balloon member 56 and sheath 16 form the inner and outer membranes of the present invention.

Figure 2:
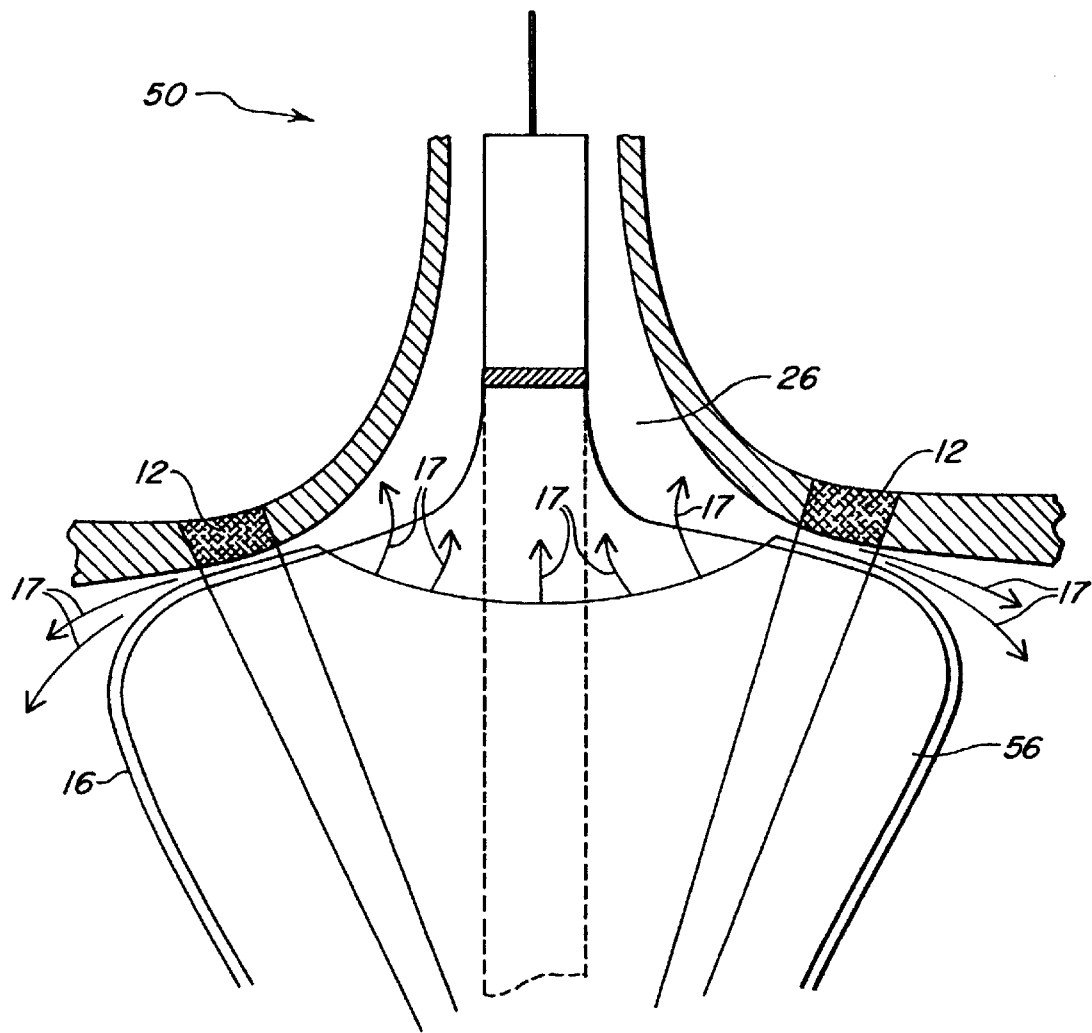
FIG. 2 is a more detailed schematic side view of the balloon catheter apparatus of FIG. 1.

In FIG. 2, the balloon catheter of FIG. 1 is shown in use. Fluid 17, introduced between the inner membrane formed by the primary balloon member 56 and the outer membrane formed by sheath 16, provides irrigation to an inner body lumen region 26. The fluid 17 can be any physiologically compatible fluid, such as saline. Once the fluid 17 is introduced into the lumen region 26, any blood or other substance remaining in the region is flushed out.

Figure 3:
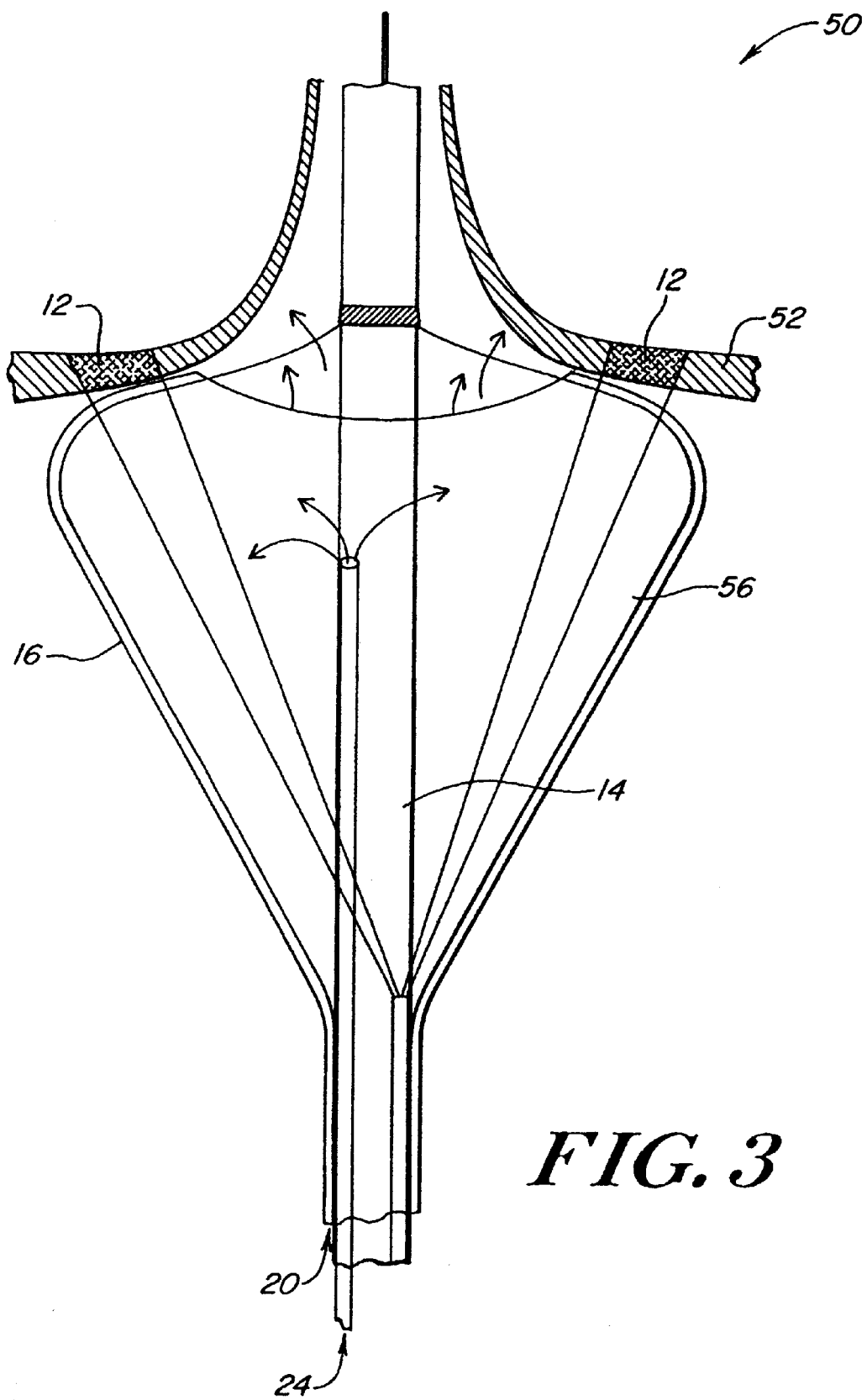
FIG. 3 shows another balloon catheter apparatus according to the invention having conduits for providing inflation fluid, and irrigation fluid to the apparatus.

Another embodiment of balloon catheter 50 is shown in FIG. 3 having two conduits 20 and 24 within the catheter 14. Conduit 20 provides irrigation fluid, such as saline, to the sheath 16. Conduit 24 provides inflation fluid, such as deuterium oxide ($D_2O$), to the primary balloon member 56.

Figure 4:
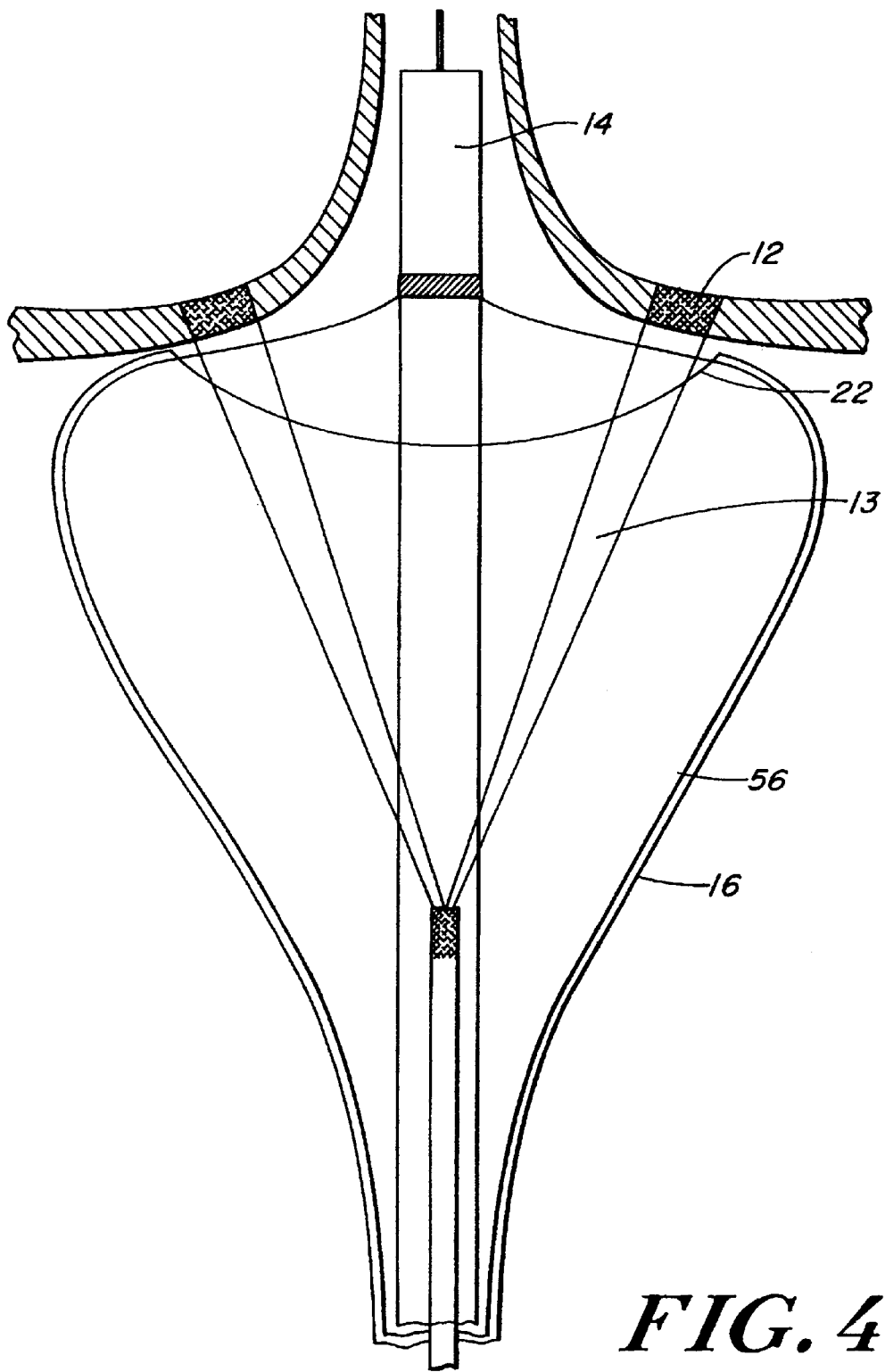
FIG. 4 shows another embodiment of the balloon catheter apparatus according to the invention having pores for providing irrigation fluid to a treatment site.

FIG. 4 illustrates another embodiment of the balloon catheter of the present invention. The opening 22 of the sheath 16 is positioned to deliver fluid 17 to the target ablation site 12. This approach allows the fluid to contact the ablation site, thereby cooling the tissue to prevent overheating or coagulation.

Figure 5:
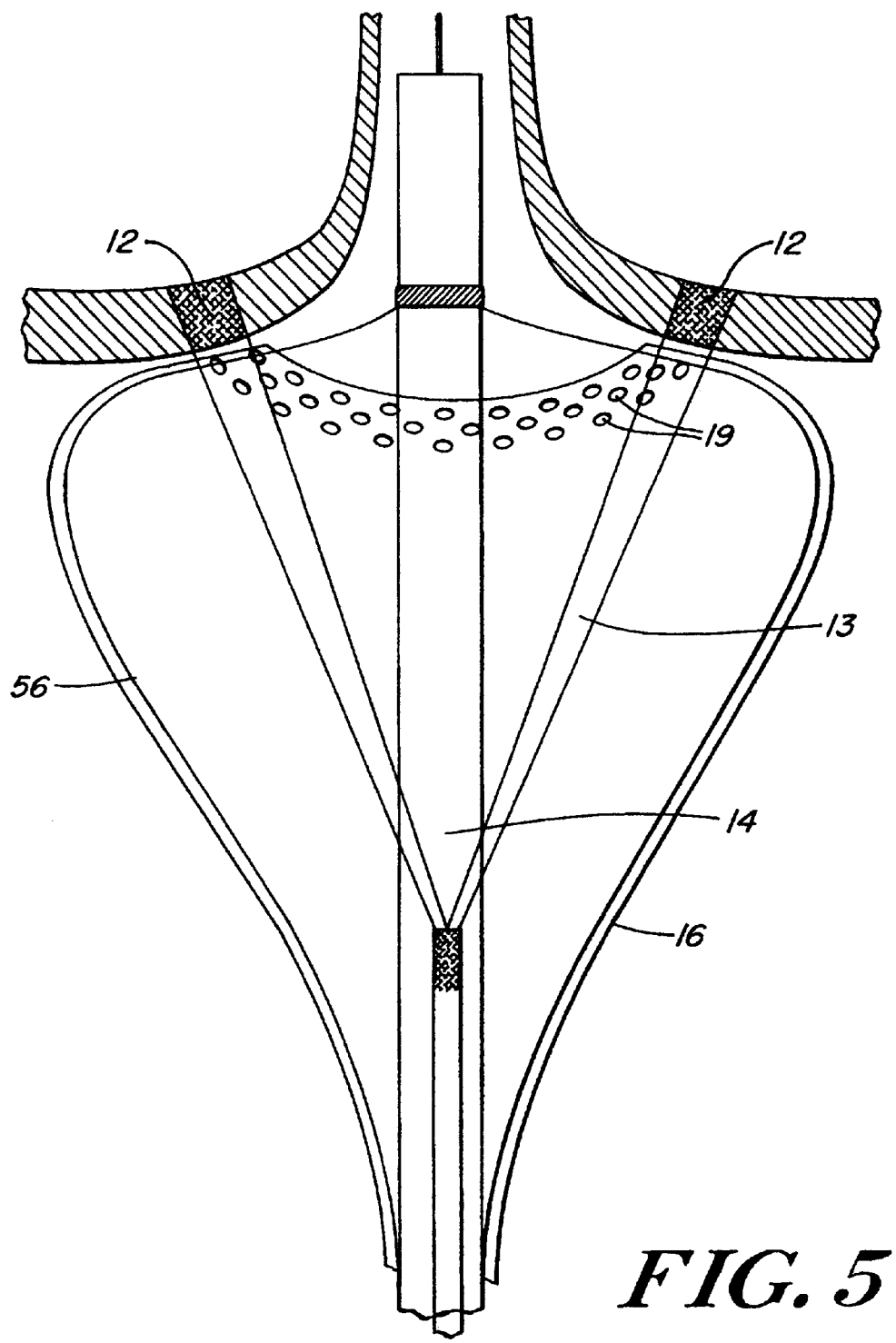
FIG. 5 shows another embodiment of the balloon catheter apparatus according to the invention having a sheath positioned to deliver fluid to a target ablation site.

FIG. 5 illustrates another embodiment of the balloon catheter of the present invention. The sheath 16 contains pores 19 for releasing fluid near or at the target ablation site 12. One having ordinary skill in the art will readily appreciate that the pores can be any shape or size. In addition, the sheath 16 can be sealed on both ends.

A person having ordinary skill in the art will readily appreciate that the size, quantity, and placement of the pores 19, and the position of the sheath opening 22 can be used in conjunction with one another to provide a desired amount of fluid to the treatment site.

In another embodiment, the primary balloon 56 is preshaped to form a parabolic like shape. This is accomplished by shaping and melting a TEFLON® film in a preshaped mold to effect the desired form. The primary balloon 56 and sheath 16 of the present invention are preferably made of thin wall polyethylene teraphthalate (PET). The thickness of the membranes is preferably 5–50 micrometers, and more preferable, 10–20 micrometers. When inflated, the diameter of the membranes is preferably in the range of 20–30 millimeters.

The balloon catheters of the present invention can be used for a variety of procedures, including laparoscopic, endoluminal, perivisceral, endoscopic, thoracoscopic, intraarticular and hybrid approaches. For example, atrial therapies can be performed by inserting an apparatus of the invention into the femoral vein. The catheter 14 having inner and outer membranes, e.g. primary balloon 56 and sheath 16, fixedly attached thereto is guided through the inferior vena cava, and into the right atrium, and if required, it is guided into the left atrium via atrial septal puncture. Left ventricular treatment can be performed by inserting flexible elongate member 32 into the femoral artery. The catheter 14 is guided through the iliac artery, the aorta, through the aortic valve and into adjacent to the left ventricle. Once the primary balloon 56 is proximate to the tissue ablation site, a solution can be injected through lumen 20 into the sheath 16 to force blood and/or body fluids away from the treatment site. An optical apparatus is then guided through catheter 14 to a position proximate to the tissue ablation site 12 and energy, e.g., laser energy, is emitted through primary balloon 56. Preferably, the composition of the primary balloon member 56 is transparent to the energy emitted through optical apparatus.

The primary balloon and sheath can be deflated by applying a vacuum that removes the fluid from the balloon. A syringe or other known methods can be used to remove the fluid. Once the primary balloon and sheath are fully deflated, the catheter can be easily removed from the body lumen.

The term lumen, including derivatives thereof, is herein intended to mean any cavity or lumen within the body which is defined at least in part by a tissue wall. For example, cardiac chambers, the uterus, the regions of the gastrointestinal tract, the urinary tract, and the arterial or venous vessels are all considered illustrative examples of body spaces within the intended meaning.

The term "catheter" as used herein is intended to encompass any hollow instrument capable of penetrating body tissue or interstitial cavities and providing a conduit for selectively injecting a solution or gas, including without limitation, venous and arterial conduits of various sizes and shapes, bronchioscopes, endoscopes, cystoscopes, culpascopes, colonscopes, trocars, laparoscopes and the like. Catheters of the present invention can be constructed with biocompatible materials known to those skilled in the art such as those listed supra, e.g., silastic, polyethylene, Teflon, polyurethanes, etc.

It should be understood that the term "balloon" encompasses deformable hollow shapes which can be inflated into various configurations including balloon, circular, tear drop, etc., shapes dependent upon the requirements of the body cavity.

The term "transparent" is well recognized in the art and is intended to include those materials which allow transmission of energy through, for example, the primary balloon member. Preferred transparent materials do not significantly impede (e.g., result in losses of over 20 percent of energy transmitted) the energy being transferred from an energy emitter to the tissue or cell site. Suitable transparent materials include fluoropolymers, for example, fluorinated ethylene propylene (FEP), perfluoroalkoxy resin (PFA), polytetrafluoroethylene (PTFE), and ethylenetetrafluoroethylene (ETFE).

Those having ordinary skill in the art will know, or be able to ascertain, using no more than routine experimentation, many equivalents to the specific embodiments of the invention described herein. These and all other equivalents are intended to be encompassed by the following claims. All publications and references cited herein including those in the background section are expressly incorporated herein by reference in their entirety.

What is claimed is:

1. A balloon catheter comprising:

a flexible elongate member;

an expandable balloon disposed about a distal portion of the flexible elongate member;

a sheath disposed about a portion of the expandable balloon and configured to inflate and deflate with the expandable balloon, the sheath having a conduit for receiving irrigation fluid from an external fluid source and at least one open end for providing irrigation fluid to a treatment site.

2. The balloon catheter of claim 1, wherein the expandable balloon has a predetermined shape in its expanded form such that, when inflated, the balloon engages and is in direct contact with the tissue of a body lumen.

3. The balloon catheter of claim 1, further comprising at least one conduit for the delivery of a fluid to the expandable balloon.

4. The balloon catheter of claim 1, wherein the conduit for the delivery of irrigation fluid is formed between the expandable balloon and the outer sheath.

5. The balloon catheter of claim 1, wherein the outer sheath is disposed about a major portion of the expandable balloon.

6. A device according to claim 1, wherein the expandable balloon, when fully expanded, provides a transmission pathway for therapeutic radiation.

7. The balloon catheter of claim 1, further comprising a plurality of pores formed in the sheath for providing irrigation fluid to a treatment site.

8. A method of positioning a catheter in vivo and providing irrigation, comprising:

introducing a catheter into a body lumen, the device having an interior lumen extending therethrough in communication with a source of fluid; and directing fluid to a first expandable balloon disposed about the catheter to position the catheter at a target site; and directing fluid between the expandable balloon and a sheath disposed about the balloon to an open end of the sheath;

whereby the balloon expands to position the catheter within the body lumen, and the sheath provides irrigation to the body lumen.

9. The method of claim 8, wherein the catheter is adapted to be positioned within a patient's heart.

\* \* \* \* \*